(12) United States Patent
Campbell

(10) Patent No.: US 10,054,505 B2
(45) Date of Patent: Aug. 21, 2018

(54) TERMINATION INSTALLATION FOR LONG CABLES

(71) Applicant: Richard V. Campbell, Havana, FL (US)

(72) Inventor: Richard V. Campbell, Havana, FL (US)

(73) Assignee: Bright Technologies, LLC, Havana, FL (US)

( * ) Notice: Subject to any disclaimer, the term of this patent is extended or adjusted under 35 U.S.C. 154(b) by 0 days.

(21) Appl. No.: 15/784,267

(22) Filed: Oct. 16, 2017

(65) Prior Publication Data

US 2018/0058959 A1 Mar. 1, 2018

Related U.S. Application Data

(62) Division of application No. 14/611,685, filed on Feb. 2, 2015, now Pat. No. 9,791,337.

(51) Int. Cl.
| | |
|---|---|
| *B66D 1/00* | (2006.01) |
| *G01L 5/04* | (2006.01) |
| *F16G 11/00* | (2006.01) |
| *D07B 1/18* | (2006.01) |
| *B66D 3/00* | (2006.01) |
| *H02G 1/14* | (2006.01) |
| *G01N 3/08* | (2006.01) |
| *G01L 5/00* | (2006.01) |

(Continued)

(52) U.S. Cl.
CPC ................ *G01L 5/04* (2013.01); *B66D 3/006* (2013.01); *D07B 1/185* (2013.01); *F16G 11/00* (2013.01); *B66D 1/04* (2013.01); *D07B 2201/1096* (2013.01); *F16G 11/02* (2013.01); *F16G 11/04* (2013.01); *F16G 11/042* (2013.01); *G01L 5/0033* (2013.01); *G01N 3/08* (2013.01); *G01N 19/04* (2013.01); *G01N 2203/0016* (2013.01); *G01N 2203/028* (2013.01); *H02G 1/14* (2013.01); *H02G 15/02* (2013.01)

(58) Field of Classification Search
CPC .. G01N 3/08; G01N 19/04; G01N 2203/0017; G01N 2203/028; G01N 2203/0016; G01L 5/0033; G01L 5/04; H02G 1/14; H02G 15/02; F16G 11/00; F16G 11/02; F16G 11/04; F16G 11/042
USPC ............................... 73/826–828; 29/857–867
See application file for complete search history.

(56) References Cited

U.S. PATENT DOCUMENTS

| | | | | |
|---|---|---|---|---|
| 2,463,116 A | * | 3/1949 | Lewis | .................. F16G 11/046 24/115 H |
| 6,561,019 B1 | * | 5/2003 | Kossat | ................. G01M 11/088 73/160 |

(Continued)

*Primary Examiner* — Jonathan Dunlap
(74) *Attorney, Agent, or Firm* — J. Wiley Horton

(57) ABSTRACT

A method for creating a composite cable having at least one high-performance termination on at least one end. A high-performance termination is added to an end of a short synthetic tensile strength member. The strength of the tensile strength member and termination is then tested. Once tested satisfactorily, the short cable is spiced onto a long cable of the same type using prior art splicing techniques. The union of the short cable and the long cable creates a "composite" cable having a high-performance termination on at least one end. In most applications it is preferable to set the length of the short cable so that the interwoven splice will exist at a desired location.

20 Claims, 10 Drawing Sheets

(51) Int. Cl.
 *B66D 1/04* (2006.01)
 *G01N 19/04* (2006.01)
 *H02G 15/02* (2006.01)
 *F16G 11/04* (2006.01)
 *F16G 11/02* (2006.01)

(56) References Cited

U.S. PATENT DOCUMENTS

| | | | | |
|---|---|---|---|---|
| 8,371,015 B2* | 2/2013 | Campbell | ............. | F16G 11/042 29/525.01 |
| 8,895,856 B2* | 11/2014 | McCullough | ........... | F16G 11/02 174/75 R |
| 8,961,061 B2* | 2/2015 | Wahlberg | ............. | F16G 11/025 403/275 |
| 9,249,577 B2* | 2/2016 | Ross | ................... | E04F 11/1859 |
| 9,379,531 B2* | 6/2016 | Boedec | .................. | H01R 4/021 |
| 9,463,849 B2* | 10/2016 | McCabe | ................. | B63B 21/20 |
| 9,791,337 B2* | 10/2017 | Campbell | ............. | D07B 1/185 |
| 9,828,068 B2* | 11/2017 | Bowen | .................... | B63B 21/20 |
| 9,835,228 B2* | 12/2017 | Campbell | ............... | F16G 11/04 |
| 2004/0083607 A1* | 5/2004 | Campbell | ............ | B29C 47/003 29/857 |
| 2007/0271897 A1* | 11/2007 | Hanna | ................... | D07B 1/162 57/238 |
| 2012/0034025 A1* | 2/2012 | Wahlberg | ............... | F16G 11/025 403/278 |
| 2012/0210926 A1* | 8/2012 | Storm, Jr. | ............... | B63C 11/26 114/337 |
| 2012/0305312 A1* | 12/2012 | McCullough | ........... | F16G 11/02 174/75 R |
| 2014/0338168 A1* | 11/2014 | Campbell | ............... | F16G 11/025 29/426.2 |
| 2015/0274260 A1* | 10/2015 | McCabe | ................ | B63B 21/20 114/44 |
| 2015/0315743 A1* | 11/2015 | Campbell | ............... | F16B 39/20 57/310 |

* cited by examiner

TERMINATION INSTALLATION FOR LONG CABLES

CROSS-REFERENCES TO RELATED APPLICATIONS

This non-provisional patent application claims the benefit of an earlier-filed non-provisional application. The parent application was assigned Ser. No. 14/611,685 (to be issued as U.S. Pat. No. 9,791,337). The parent application listed the same inventor.

STATEMENT REGARDING FEDERALLY SPONSORED RESEARCH OR DEVELOPMENT

Not Applicable.

MICROFICHE APPENDIX

Not Applicable

BACKGROUND OF THE INVENTION

1. Field of the Invention

This invention relates to the field of tensile strength members. More specifically, the invention comprises a method for creating a long tensile strength member with a high-performance termination or terminations that can be pre-tested using equipment that is limited to testing shorter tensile strength members.

2. Description of the Related Art

Tensile strength members must generally be connected to other components in order to be useful. A flexible cable provides a good example. The cable must generally include some type of end-fitting so that it can be transmit a load. For example, a cable used in a hoist generally includes a lifting hook on its free end. This lifting hook may be rigged to a load. The assembly of an end-fitting and the portion of the cable to which it is attached is generally called a "termination."

A tough steel lifting hook is commonly attached to a wire rope to create a termination. A "spelter socket" is often used to create the termination. The "spelter socket" involves an expanding cavity within the end-fitting. A length of the wire rope is slipped into this cavity and the individual wires are splayed apart. A liquid potting compound is then introduced into the expanding cavity with the wires in place. The liquid potting compound transitions to a solid over time and thereby locks the wire rope into the cavity.

The potting compound used in a spelter socket is traditionally molten lead and—more recently—is more likely a high-strength epoxy. However, the term "potting compound" as used in this description means any substance which transitions from a liquid to a solid over time. Examples include molten lead, thermoplastics, UV-cure or thermoset resins (such as two-part polyesters or epoxies). Other examples include plasters, ceramics, and cements. The term "solid" is by no means limited to an ordered crystalline structure such as found in most metals. In the context of this invention, the term "solid" means a state in which the material does not flow significantly under the influence of gravity.

Terminations on wire rope are quite common in hoists and cranes. These terminations are well understood and their performance and reliability have been established over many decades. In recent years the opportunity to replace wire ropes with modern, high-strength synthetic cables has arisen. Many different materials are used for the filaments in these synthetic cables. These include KEVLAR, VECTRAN, PBO, DYNEEMA, SPECTRA, TECHNORA, ZYLON, glass fiber, and carbon fiber (among many others). In general the individual filaments have a thickness that is less than that of human hair. They also tend to have low surface friction. They are quite different from steel wires.

Terminations, are used for synthetic filament cables, but they assume a different form than those used for wire rope. Synthetic filament cables tend to be made by braiding multiple strands together. While the individual filaments are made using various modern processes, the construction of the cable itself tends to follow the patterns established for natural-fiber ropes many years ago. Perhaps not surprisingly, the methods used to create a termination tend to follow the old patterns for ropes as well.

FIGS. 1-2 shows a traditional method for adding a termination to one end of a synthetic cable. Cable 10 is made from advanced high-strength synthetic filaments. It is known to join multi-stranded cables using weaving or splicing methods. In these methods, connections are made by interweaving strands of one section of cable with strands of another section of cable (sometimes the sections lie in the same cable and sometimes they do not).

FIG. 1 shows an exemplary prior art operation. Cable 10 includes eight individual strands of synthetic filaments. Each strand may contain thousands or even millions of individual filaments, but the prior art weaving operations do not typically break the cable down beyond the strand level. The depiction of cable 10 is representative rather than entirely accurate. The example shown has 8 separate strands. The strands would typically be interwoven with 2 pairs of strands in a left-hand helix and two pairs in a right-hand helix.

The objective of the example shown in FIGS. 1 and 2 is to weave a length of the cable back on itself to form an "eye" on the cable's end. Considerable mechanical skill and dexterity is required to form an eye on the end of a cable and in other instances to join lengths of cable together. However, persons having these skills are commonly found in industries where large cables are used. Further, the strength and reliability of cable splices made by such persons are well understood and accepted. As a result, it is readily accepted that these proven methods of connection do not require pretesting and can even be done in the field, in a non-controlled environment, by trained personnel. This is even true for critical applications. This has been the standard method of termination since inception, and it makes up over 99% of the entire industry of long synthetic fiber cables. Thus, there is considerable standardization, knowledge, and field support for such a method of termination.

In FIG. 1, a length of strands proximate the cable's end is unwoven to create separated strands 14. The end of the cable is bent into a loop or bight, sometimes around a reinforcing element such as thimble 12. FIG. 2 shows the continuation of the operation. The weave of the strands within the cable is loosened so that separated strands can be threaded back into the cable in a prescribed pattern. Interwoven section 24 is thereby created. The loose ends of separated strands 14 are typically cut off (after a sufficiently long interwoven section 24 has been created) and taped or otherwise secured.

The result is eye splice 16 on one end of cable 10. When produced by trained personnel, the eye splice does work and it is considered an efficient and reliable means of termination. In this context the term efficiency means the ratio of the breaking stress of the complete cable with the termination attached versus the breaking stress of the cable without a stressed area such as in the middle of the cable. A perfectly efficient cable would have an efficiency of 100%, including the termination. On synthetic fiber cables, achieving this or nearly this efficiency is commonly possible with many forms of prior art splices.

Although the eye splice is strong, it is ill-suited to many applications. For example, while one could use an eye splice to attach a lifting hook to the end of a hoist line, the eye splice is unable to withstand battering forces very well. In addition, the diameter of the eye splice will be too large in many instances. It would be advantageous to instead connect a hook or other device directly to the synthetic cable, analogous to the way a spelter socket is connected to a wire rope. Fortunately, the technology to create such terminations exists.

The prior art approaches to adding a termination to a synthetic cable are explained in detail in commonly-owned U.S. Pat. No. 7,237,336, which Is hereby incorporated by reference. The terminations can be added to the cable as a whole or some sub-component of the cable such as a strand. Commonly-owned U.S. Pat. No. 8,371,015 explains how multiple terminations may be attached to multiple strands of a larger cable. This too is incorporated by reference.

In order to gain a strong and repeatable result, the addition of a termination directly to a synthetic cable must generally be done under highly controlled conditions such as found in a factory. This is particularly true of medium to large end fittings configured for a cable having an overall diameter of greater than 20 mm and sometimes being considerably larger. In fact, those skilled in the art recognize that terminating larger synthetic cables is exceptionally difficult to master in even a highly controlled environment. Unlike most metal strength members, achieving an efficient and repeatable result requires very stringent control of the process, highly skilled personnel and precise processing.

An end-fitting is commonly attached to a larger synthetic filament cable by use of a potting compound. Liquid potting compound (such as an epoxy or a polyester) is added to a cavity in the fitting after a length of filaments has been placed within the fitting. It is preferable to hold the components in a stable configuration while the potting compound cures—which may take 12 hours or more. Temperature and other variables are preferably controlled during this process, as are the properties of the potting compound itself. The potting compound may be added to the cavity in a variety of ways, including pre-wetting, infusing, etc.

The process of attaching an end fitting to a synthetic cable produces a wider performance variation than is typical for steel cables or for spliced techniques on synthetic cables. In fact, the creation of an advanced termination on an end of a synthetic cable will often represent the weakest link in the whole system. As such, in many instances it will be necessary to test the strength of the completed termination before it is used.

Exemplary applications include hoisting cables and mooring cables where a known and predictable strength is very important. This requirement creates challenges in the field of synthetic-filament cables since conventional tensile testing equipment used in the industry is (1) limited in strength and (2) limited in length. A typical large test frame can pull loads of about 1,000 tons. The length of such a test frame is only about 20 meters though. Longer test frames do exist (some over 100 meters) but they are very rare. When tensile members are made longer than the length of the readily available test frame, they are rarely able to be tested properly given the practical constraints that exist in industry. This creates limitations on what can be tested and impacts logistics on any large or remotely used tensile members requiring specialty terminations.

It is desirable to use synthetic filament cables to replace steel and other conventional cables, but in order to do so the synthetic filament cables must have an equivalent useful length. Many large diameter applications are well beyond the typical test bed length, such as 500 or even 1,000 meters as an example. In fact, most large and/or long cables will not fit in any test bed in the world. This complication does not present a serious issue for existing steel or synthetic cables using conventional technology because highly standardized methods and devices have been developed and proven to be reliable over the last century.

By comparison, it is not commonly possible to achieve the same level of efficiency, reliability, and repeatability with many of the more compact, mechanical, versatile synthetic cable methods of termination such as porting sockets, resin terminations, composite terminations, or spike-and-cone type frictional arrangements, etc. These types of terminations tend to put far greater stresses in a smaller area, meaning there is much less room for operator error and the efficiency can often be reduced if not handled properly. Further, these types of terminations on synthetic cables have by comparison a limited history, limited use, limited standardization and training, and introduce a significantly greater need for control over the process in order to achieve a repeatable result.

On a synthetic cable, known splicing techniques may not be suitable for long lines and are often not ideal from a termination perspective. For example, there is often a need for a termination analogous to those used for wire rope. Examples include termination with a hard end such as a hook, a threaded stud, a small eye, or a clevis on the end of a spelter or resin socket, etc. Such hard, versatile, and generally compact ends are well known and thus a desirable option in most industries where large and/or long cables are used. As an example, an offshore steel crane wire would typically have a very compact, potted socket made from steel and including a clevis or eye connection. As with splices used for synthetic fiber cables, these versatile forms of terminations are well established, standardized, trusted, and produced in the field with technicians that are trained in the process. Therefore high load testing in a proofing bed is not generally necessary. However, when considering a high performance synthetic cable, spliced eyes do not provide the same level of functionality or versatility as those from less proven methods.

The proposed method creates a safe and reliable means to apply and validate the performance (pre-test) of a more desirable termination on such long synthetic cable applications. FIG. 3—a sectional view—shows an example of an advanced termination. Anchor 18 includes an internal cavity 20. A length of strands from cable 10 is placed within this cavity. Preferably the strands are splayed apart in some form of expanding cavity (though other techniques may be used). A liquid potting compound is placed within the cavity (either before, during, or after the strands are added).

The liquid potting compound transitions to a solid over time to create potted region 22. Once solidified as shown, the strands within potted region 22 are locked in place and anchor 18 is secured to the end of the cable. Some feature tor transmitting a load to the cable is typically included. In this example loading feature 21 assumes the form of a loop.

Other classes of advanced terminations can be made without using a potting compound to secure the cable strands to the anchor. FIG. 10 shows an assembly that is commonly referred to as a "spike and cone" termination. A length of strands is splayed apart in cavity 20 as for the potting example. However, rather than using potting compound, they are mechanically secured. Cone 62 is introduced into the center of the strands. Compression plug 64 is then screwed into the open end of anchor 18 via threaded engagement 66. The strands are then mechanically clamped in place.

It is possible to combine the prior art approaches—such as by using potting compound in the spike-and-cone configuration of FIG. 10. In addition, anchor 18 can be made quite tough. As an example, the anchor may be made of stainless steel so that it can endure an abusive environment. Such a termination is advantageous in many instances where a synthetic cable is used.

Countless forms of synthetic fiber cable terminations can be conceived, including those made entirely of composites for example. Any such versatile termination that is not a splice, and especially these which are more compact in nature, have many potential limitations as covered previously. These limitations create the absolute need for production in a controlled setting (which is not in the field).

Given the above, the present industry issue exists: Large ropes are utilized in the field, often in remote areas, and they often need to be re-terminated. Going back to the offshore crane example, if a crane line is damaged in the ocean, there must be an immediate remedy to get back to work. Removing the line and shipping the cable to its original factory for re-termination is not a feasible option. Reliable field termination of many forms exist for steel wire today, but they do not exist for synthetic cable. If using a synthetic cable and the termination is anything other than a splice, it requires both a controlled setting and most often proof testing to ensure safe and reliable use. This very fact has prevented synthetic cables from being utilized where a more versatile or compact termination is needed. The present invention presents a solution to this problem, among other problems.

BRIEF SUMMARY OF THE PRESENT INVENTION

The present invention comprises a method for creating a composite cable having at least one advanced termination on at least one end. An advanced termination is added to an end of a short synthetic tensile strength member. The strength of the tensile strength member and termination is then tested. Once tested satisfactorily, the short cable is spliced onto a long tensile member of a comparable type using prior art splicing techniques. The union of the short tensile member and the long tensile member creates a "composite" cable having an advanced termination on at least one end. In most applications it is preferable to set the length of the short cable so that the interwoven splice will exist at a desired location.

REFERENCE NUMERALS IN THE DRAWINGS

Figure 1:
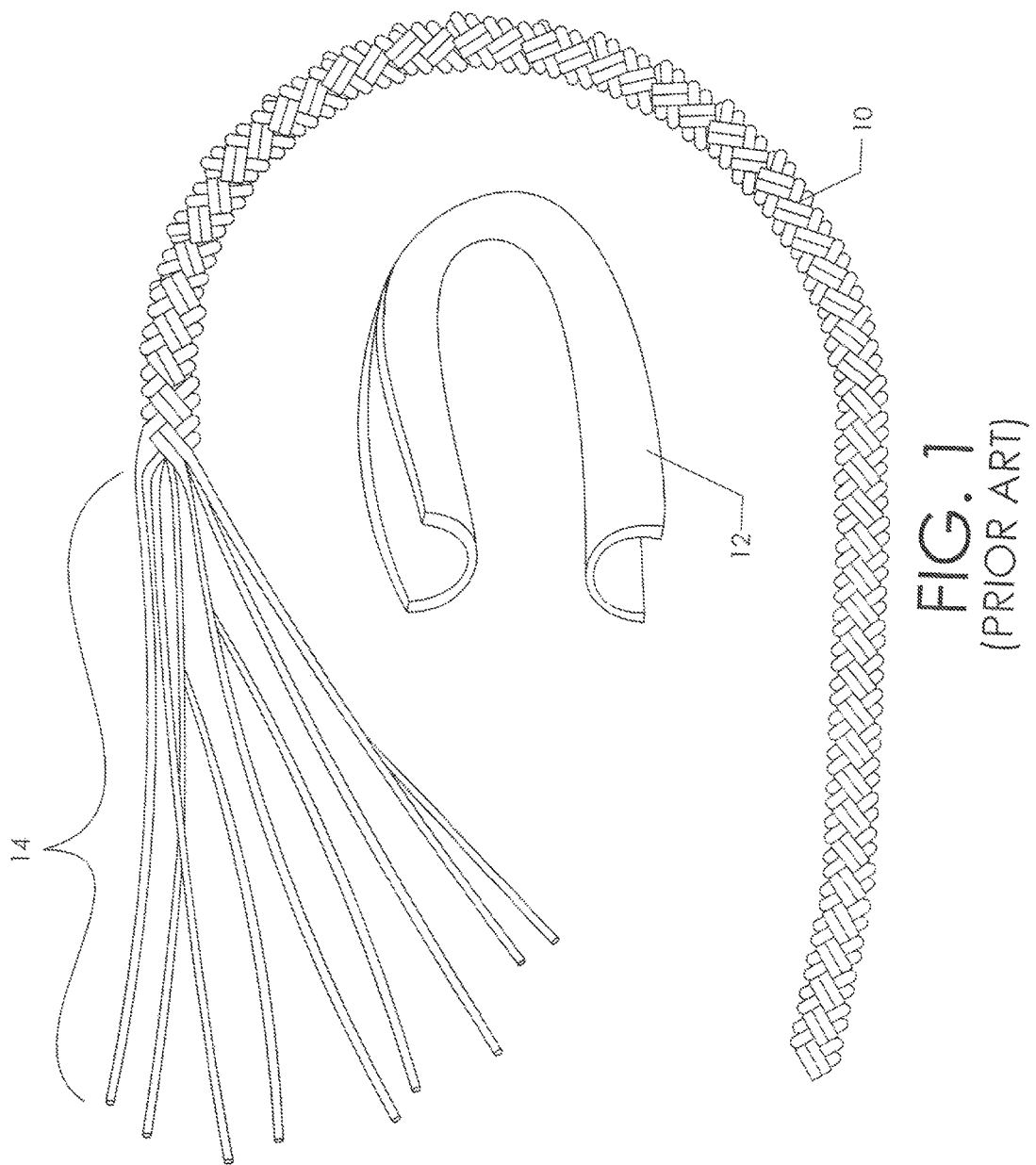
FIG. 1 is a perspective view, showing the creation of a prior art eye splice.

10 cable
12 thimble
14 separated strands
16 eye splice
18 anchor
20 cavity
21 loading feature
22 potted region
24 interwoven section
26 short cable
28 drum
30 test loading device
32 oil platform
34 crane
35 boom
36 composite cable
38 sea surface
40 sea floor
42 payload
44 max hook height
46 lower splash boundary
48 drum
50 top sheave
52 dragline crane
54 boom
56 lifting crane
58 dragging cable
60 bucket
62 cone
64 compression plug
66 threaded engagement

DETAILED DESCRIPTION OF THE INVENTION

The present invention applies to virtually any type of tensile strength member using synthetic filaments as the core load bearing elements. This would include common device terms such as ropes, cables, cords, etc. Cables are used as examples of elastic strength members in the embodiments described. While the present invention is not applicable to steel wire cables, it is highly applicable to synthetic fiber cables that are used principally for load-bearing purposes, and the like.

The main concept of the invention is to create a "short" tensile strength member with one or more advanced terminations attached. The term "advanced termination" is defined to mean any component that can be attached directly to a synthetic cable without using interweaving techniques.

The term includes anchors attached by potting a length of filaments into an internal cavity and spike-and-cone type anchors, among others. The "short" assembly is tested so that its useful working load is known for certain. The "short" assembly is then joined to a "long" tensile strength member using prior art interweaving techniques. The result is a composite cable whose overall performance is known by (1) the results of the testing done on the "short" assembly, and (2) years of accumulated practical understanding of the performance of interwoven splices. The terms "short" and "long" are of course vague and they will be defined in the context of the invention.

Figure 4:
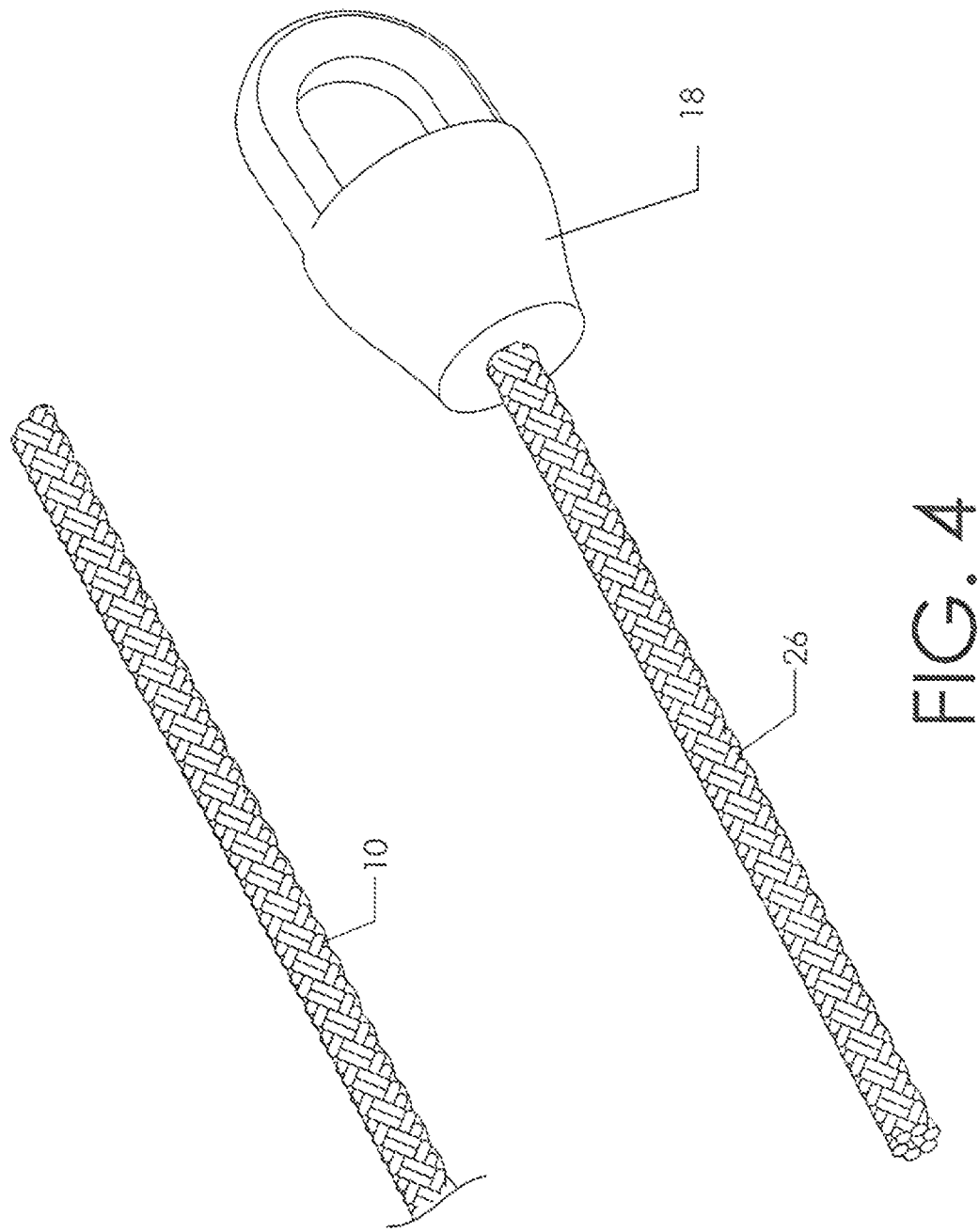
FIG. 4 is a perspective view, showing a terminated short cable made according to the present inventive process.

FIG. 4 shows two components of a composite cable before they are joined together. Short cable 26 includes an advanced termination that has been attached to one end as described previously. Cable 10 in this example is a "long cable" with no attached hardware. In this example both cables are made of braided strands. The drawing does not depict the braided construction completely accurately, since it is quite complex, but the lines show that some of the braid components are twisted in one direction and some are twisted in the opposite direction.

Figure 5:
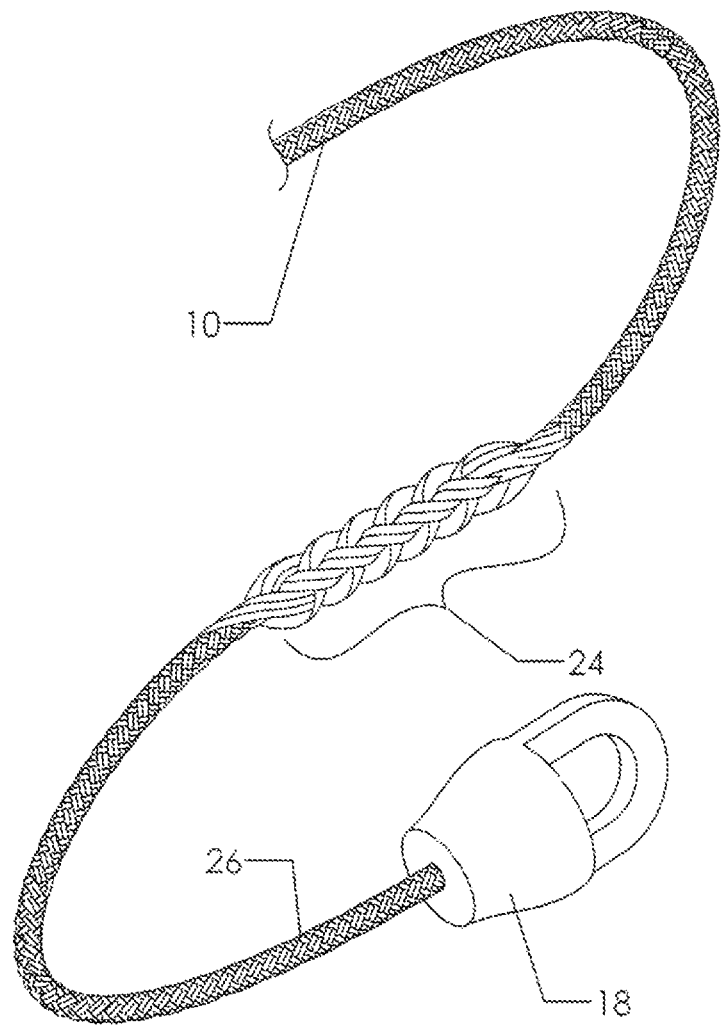
FIG. 5 is a perspective view, showing a composite cable made according to the present invention.

It is possible using prior art techniques to create an interwoven, interlocking, or otherwise gripping splice between these two pieces of cable. FIG. 5 shows the two cable segments joined together by an interwoven splice. Short cable 26 and long cable 10 are joined together by interwoven section 24. The result is a much longer "composite" cable.

The terms "short" and "long" are relative to each other. A typical "short" cable might range from as short as 5 meters to as long as 100 meters. In some rare cases this may be even longer. A "long" cable might range from 50 meters up to several km in length. When the terms "short" and "long" are used in this description, the reader should understand that the "long" cable is typically 4 or more times longer than the short cable. The determination of the length of each component is often dictated by the availability of testing equipment for evaluating the performance of the short cable, and the actual application, as will be explained subsequently.

A detailed explanation of the prior art interweaving techniques used in cable splices is beyond the scope of this disclosure, but the reader may benefit from some general explanation. An interwoven splice is applicable to any synthetic tensile strength member made of multiple strands, so long as the strands are arranged in some ordered fashion. Cable strands are generally braided, twisted, or laid in a helical fashion. Generally, however braids such as a twelve strand are most common due their ease of splice-ability. A permanent joint can be created between two cables (or two parts of a single cable) by partly untwisting the strands and then interweaving them. Interwoven splices can be used to form a loop or eye on an end of a cable. They may also be used for joining the ends of two cables together (either directly or by forming an eye on one cable end that is interlocked with an eye on the other cable end).

In general, a section of completely unwoven strands are created on the end of one cable and a section of loosened (yet not unwoven) strands are created on the end of a second cable. The completely unwoven strands on the first cable are then woven into the voids between the loosened strands on the second cable in a prescribed and repetitive fashion. A specified number of weaves are created. Any excess material from the unwoven strands of the first cable is then removed and the free ends are secured by any suitable method, such as taping or whipping.

The creation of a proper interwoven splice is a skilled job that is customarily carried out by a trained rigging specialist. Fortunately, such specialists are common within the industries needing high-strength synthetic fiber cabling. When properly done, an interwoven splice can be capable of maintaining the cable's full breaking strength.

The interweaving techniques are very old, as most were developed in the age of sailing ships. The performance of such interwoven splices is well understood and perhaps as importantly—very well trusted within the industries where they are used. Readers wishing to know more of the details of accepted interwoven splicing techniques are referred to The Splicing Handbook, 2nd Edition, published by International Marine (ISBN 0-07-135438-7).

Figure 3:
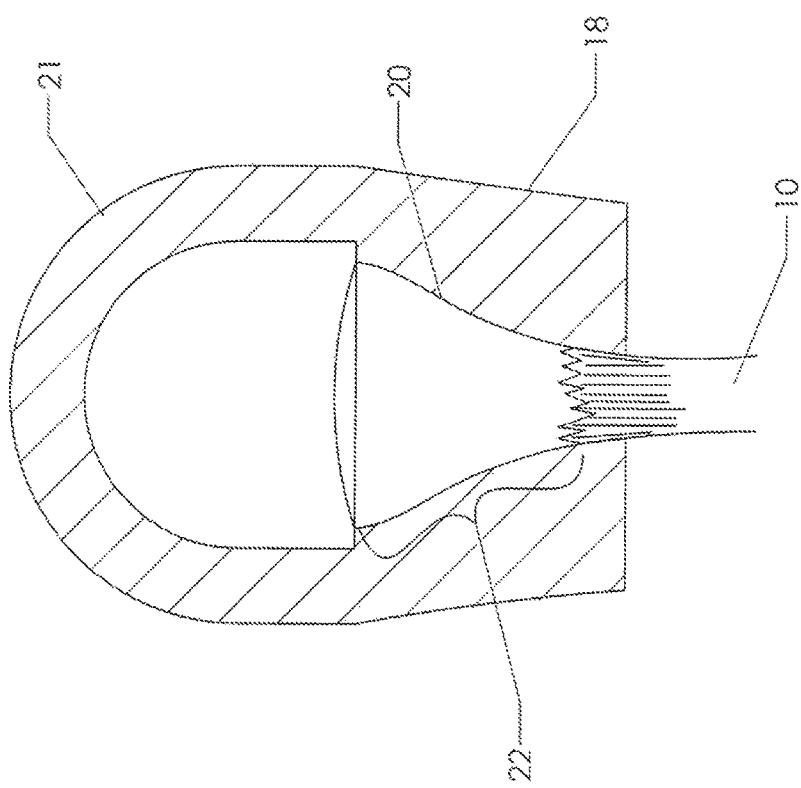
FIG. 3 is a sectional elevation view, showing the addition of a high-performance termination to one end of a synthetic cable.
Figure 10:
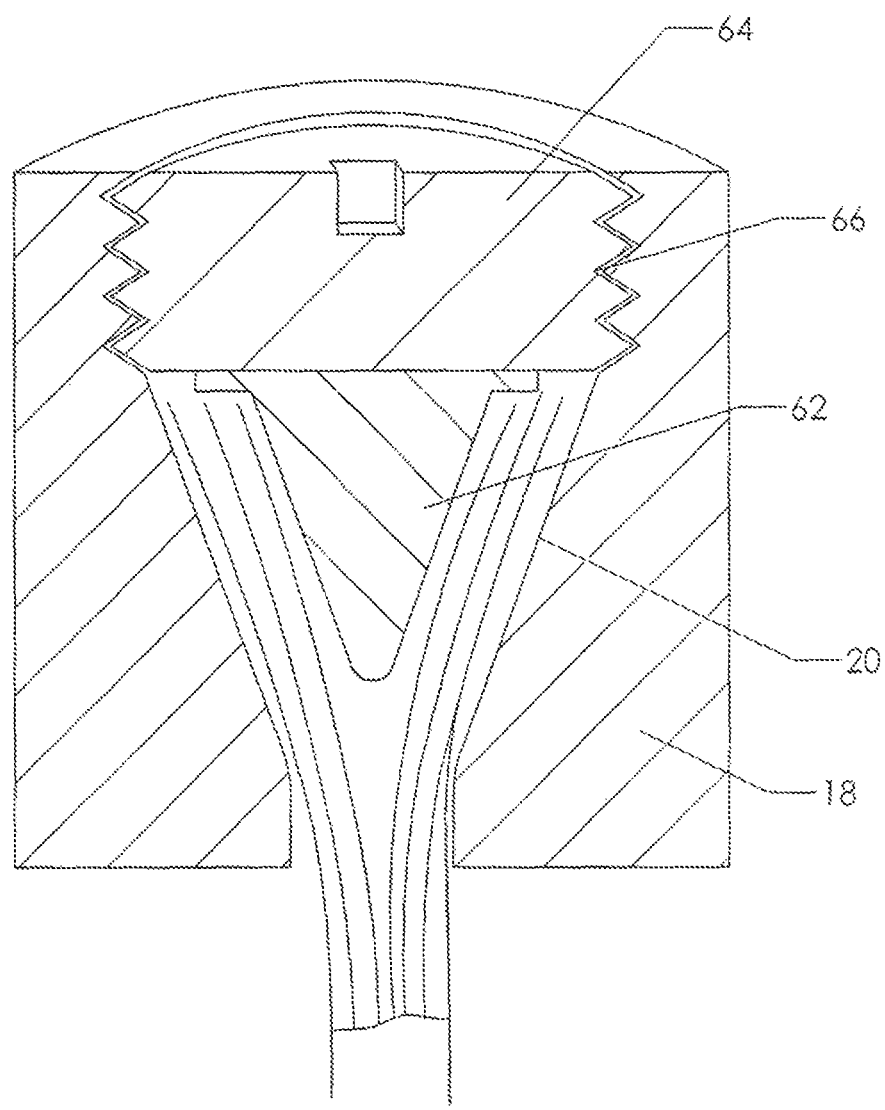
FIG. 10 is a sectional elevation view, showing another type of high-performance termination.

Terminations such as shown in FIGS. 3 and 10 are preferably created under controlled conditions. This will typically be a factory production facility, though a smaller scale facility could be set up to handle it as well. In the case of a potted termination, cable and anchor alignment is preferably maintained over the cure time of the potting compound. This may take a day or even longer. In addition, the strand alignment within the cable also dictates the creation of a constrained length of cable extending out of the anchor.

Potting compound mix ratios are important, as are other factors such as the ambient temperature. Preferably many conditions are controlled in order to create a strong and repeatable result. Even with the best process controls, however, these less conventional, compact forms of terminations are inherently less proven and much more susceptible to breaking efficiency loss and general breaking scatter due to processing inconsistencies or errors. Thus a critical element of quality control for such terminations is the proof testing process, and this is especially needed on critical applications such as lifting, securing, towing, mooring, etc.

Figure 6:
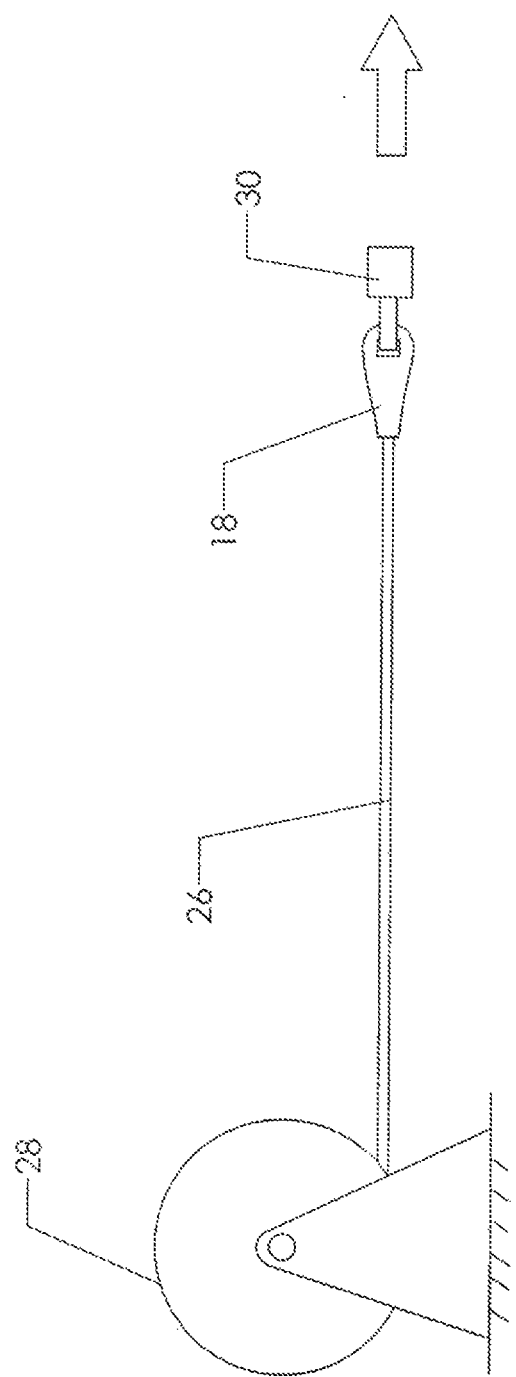
FIG. 6 is an elevation view, showing an exemplary test rig used to test a short cable made according to the present invention.

FIG. 6 schematically depicts one of many possible testing rigs for a short cable 26 with an attached anchor 18. Cables made of synthetic filaments tend to have low surface friction and are not easy to grip. It is often important to apply very high tensile loads in the test. In many cases this will be a significant fraction of the calculated breaking strength of the cable. Thus, it is often not possible to apply this amount of tension through a fixture that simply grips the cable's exterior. Likewise, it is not desirable to knot a portion of the cable around a loading fixture since the knot will drastically reduce the cable's strength.

FIG. 6 shows one end of short cable 26 being wrapped around drum 28. It is possible to wrap several turns of the cable around a drum of suitable diameter and thereby secure the cable's free end without over-stressing it. Test loading device 30 is attached to anchor 18 using a hook or similar feature. Tension may then be applied through test loading device 30 while dram 28 is held in position. In another version, test loading device 30 could be held in a fixed position while torque is applied to the drum. Other testing fixtures are obviously possible and the example provided is by no means limiting.

Alternately as could be imagined by those skilled in the art, if the short cable is able to be tested within the load frame, a dummy or sacrificial end such as a spliced eye or potted termination could be applied to the opposing end. In such a case a conventional fixed point cable could be used in place of the drum, and this dummy or sacrificial end could then be removed if desired.

However loaded, the result of the test is that the cable can be certified as having been loaded to a specified amount with no problem resulting. Any defect in the manufacturing of the components or the assembly process may thereby be reliably detected.

Returning now to FIG. 5, the reader will recall that short cable 26 is joined to long cable 10 using known interweaving ("splicing") techniques. When properly executed, interwoven section 24 will have a break strength equal to or greater than the break strength of the cable itself. As explained previously, the break strength of the advanced termination (created by attaching anchor 18), depending on the design and method of manufacture, will commonly be somewhat less than the break strength of the cable (though possibly quite close).

Thus, in the assembly of FIG. 5 the "weak link" is the termination point. However, the termination has been tested (such as by the rig of FIG. 6) and certified to exceed a specified break strength. Thus, the assembly as a whole in FIG. 5 (a "composite cable") may be certified as having a break strength in excess of the tested amount.

At this point it may be natural to wonder why a composite cable is needed and ask instead why one would not simply attach the anchor to one end of long cable 10 and dispense with the need for the interweaving process. There are several reasons why such an approach would be undesirable. First long cable 10 is often extraordinarily long. It is not unusual for such a cable to be 15,000 meters or more in length. Such a cable is often rolled onto a large and heavy drum. It is not a simple matter to move such a large cable and bring it into a controlled facility for the addition of an anchor.

Second, it is generally true that a test such as shown in FIG. 6 must be carried out by a device on one end of the cable that engages the anchor and a device on the other end that engages the free end of the cable. Thus, the length of the cable being tested determines the length of the apparatus required to test it. For example, it is not preferable to engage a synthetic cable at some mid-point and then apply considerable tension. The test of FIG. 6 shows the free end of the cable being wrapped around a drum and secured. Five or ten turns may be needed to adequately secure the cable to the drum. Applying the drum-wrap at the mid-point of the cable would likely produce slippage between the cable strands and a degradation of the cable's performance. Thus, the cable is preferably tested by holding it at its ends and applying tension.

Therefore, the distance between the drum and the test loading device 30 will determine the length of the cable that can be tested. A large facility might have a test fixture that is 50 meters in length, but a longer fixture is rare. It is also not generally feasible to have a "mobile" end point such as a moving vehicle. Static testing of such cables often requires huge tensile forces—such as 250,000 pounds. No vehicle remains stationary during the application of such a force. Even static structures must be carefully designed to withstand such forces.

Since one of the significant features of the present invention is the actual testing of the advanced termination, it is important for short cable 26 to have only a moderate length. Preferably it is less than 100 meters in length and may in fact be much shorter. The length selected for short cable 26 will of course determine the location of the interwoven section.

Returning now to FIG. 5, the reader will note that interwoven section 24 is thicker than the other portions of the composite cable. This added thickness can cause problems when running the interwoven section over pulleys or other devices. Thus, the location of the interwoven section is preferably considered when creating a composite cable. The pulleys and other feeding devices can be designed to accommodate the added thickness of interwoven section 24. However, it is generally undesirable to have interwoven section 24 pass around a pulley or other bend while it is heavily loaded.

Figure 7:
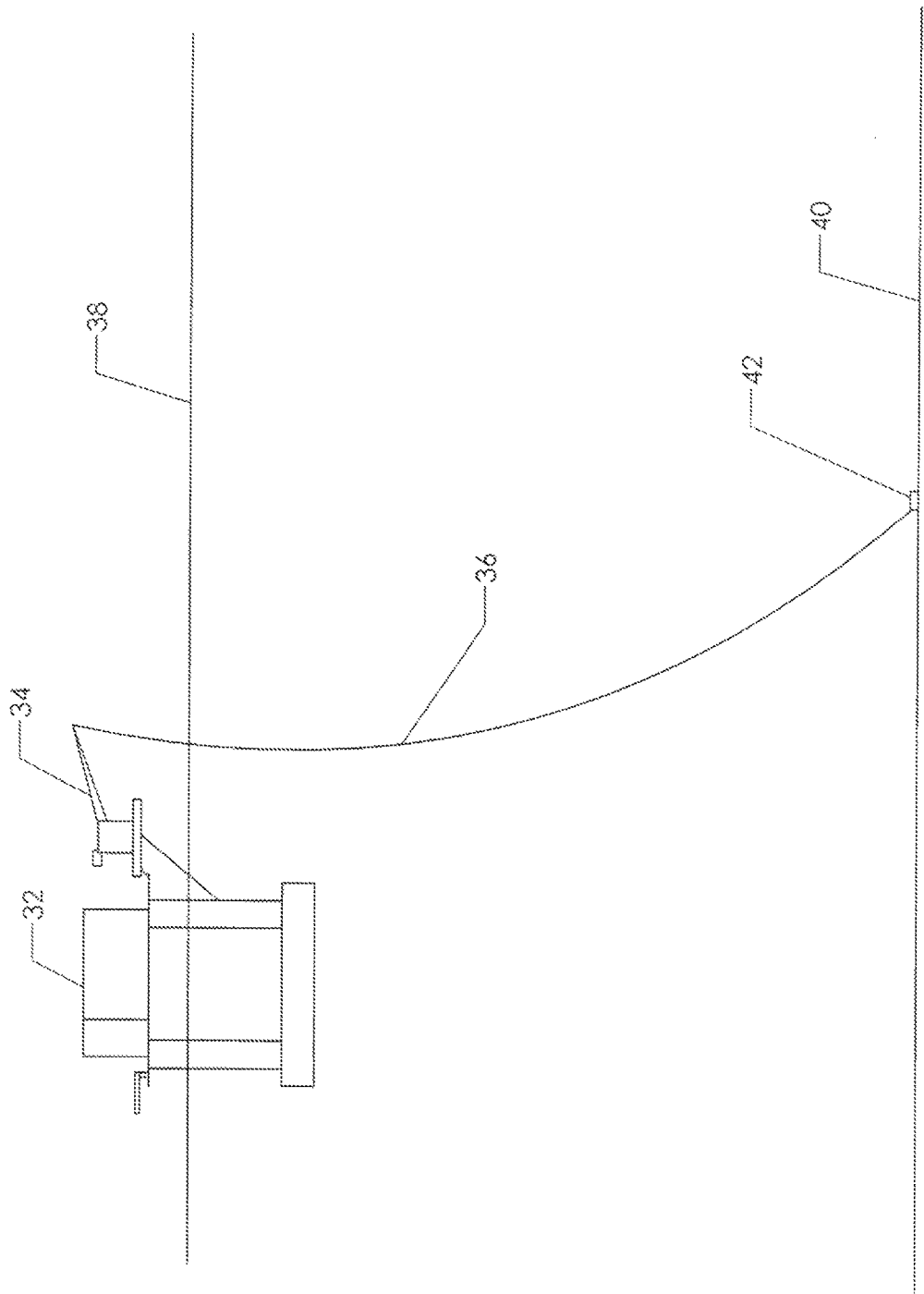
FIG. 7 is an elevation view, showing an inventive cable in use on an oil platform.

FIG. 7 shows one representative application for a composite cable made according to the present invention. Crane 34 is mounted on offshore oil platform 32, well above sea surface 38. Composite cable 36 extends down into the water where it is connected to pay load 42 resting on sea floor 40. In this simple example, sea floor 40 might lie at a depth of 3,000 meters below sea surface 38. It is apparent from this diagram that the interwoven section of composite cable 36 lies well underwater at this point and in fact will be quite close to sea floor 40.

Figure 8:
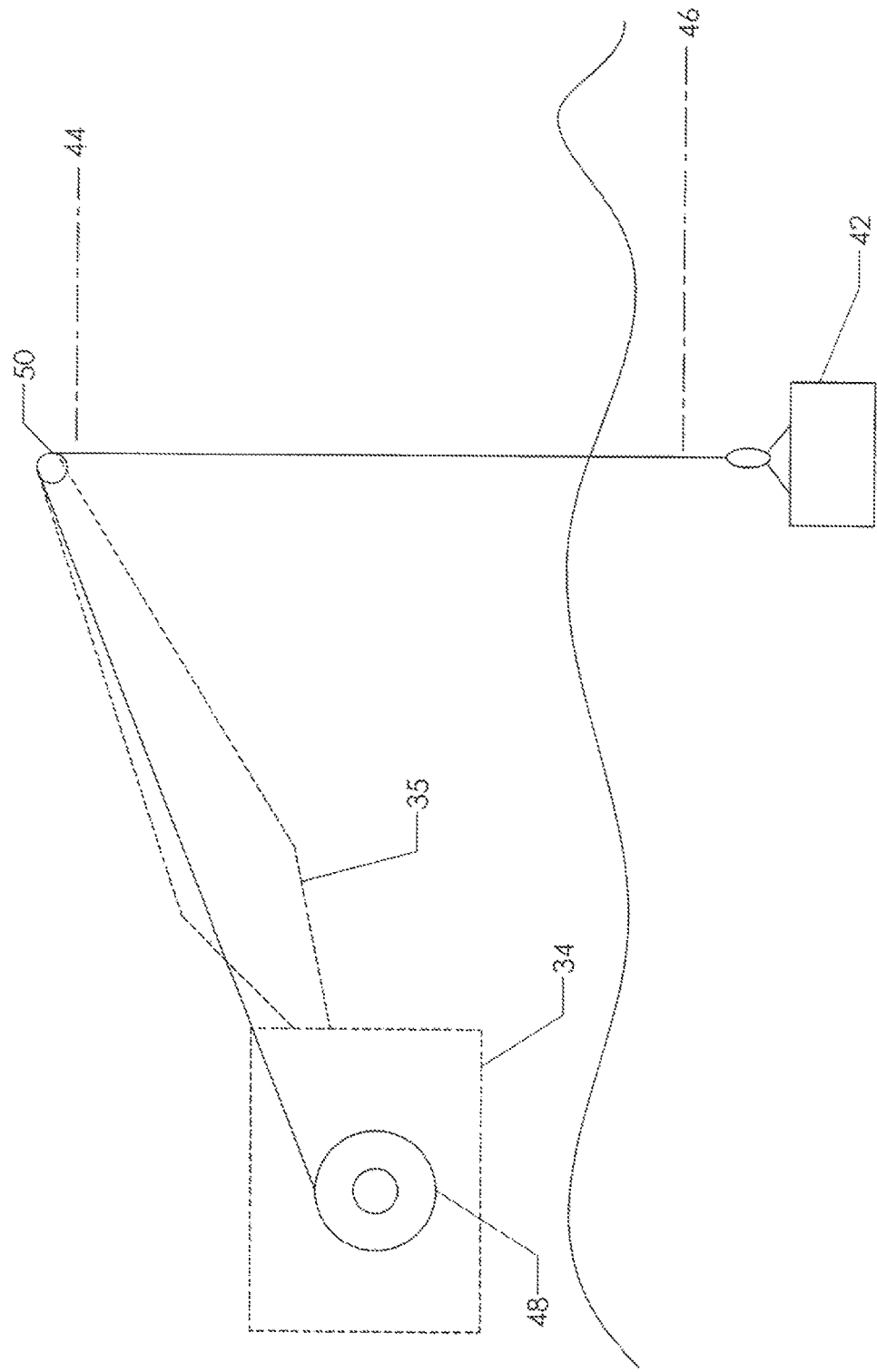
FIG. 8 is an elevation view, showing an inventive cable being used to hoist a load out of the water.

However, when the crane reels in composite cable 36 the interwoven section will be pulled up toward the surface. FIG. 8 shows a closer view of crane 34. Crane 34 includes tension-carrying drum 48 which is used to pay off and reel in composite cable 36. In the version shown the tension-carrying drum is also used to store the cable. As those skilled in the art will know, in other examples a tension-carrying drum is supplemented by a second drum that is used to store the cable. Boom 35 mounts tip sheave 50, over which the cable passes. Max hook height 44 represents the maximum height to which the crane can lift the payload.

As those skilled in the art will know, the load imposed on the cable by payload 42 varies substantially depending upon whether the payload is immersed in the sea or lifted clear into the air. The weight of an object immersed in water is reduced by the weight of the volume of water displaced by the object. This concept is generally referred to as Archimedes' Principle. For a typical solid structure, its weight in water is less than ½ its weight in air.

Crane designers working in offshore applications carefully consider Archimedes' Principle. The water's surface is not stationary in offshore applications but rather moves with each passing swell. Thus, there is often not a clearly defined surface level. Instead, the engineers refer to a "splash zone" having a lower boundary and an upper boundary. They consider that the payload could be lifted free of the water anywhere within this "splash zone."

It is the lower extreme of the splash, zone that is often most important. Lower splash boundary 46 is shown in FIG. 8. At any time that payload 42 is lifted above this height it might in fact be free of the water and the composite cable would then be subjected to the full weight of the payload in air.

Designers in this off-shore application might decide that the interwoven section of the composite cable needs to be on drum 48 before payload 42 is lifted above lower splash boundary 46. They may further conclude that the interwoven section needs to have five turns on the drum between itself and the paid off portion of the cable when payload 42 is lifted above lower splash boundary 46. These criteria represent examples of design constrains that determine the length of short cable 26 in a particular application.

Other designers working in a similar environment might prefer that the interwoven section never pass through top sheave 50. In that case the short cable length would be determined as the length necessary to provide adequate lifting height for the payload while keeping the interwoven section below top sheave 50.

Figure 9:
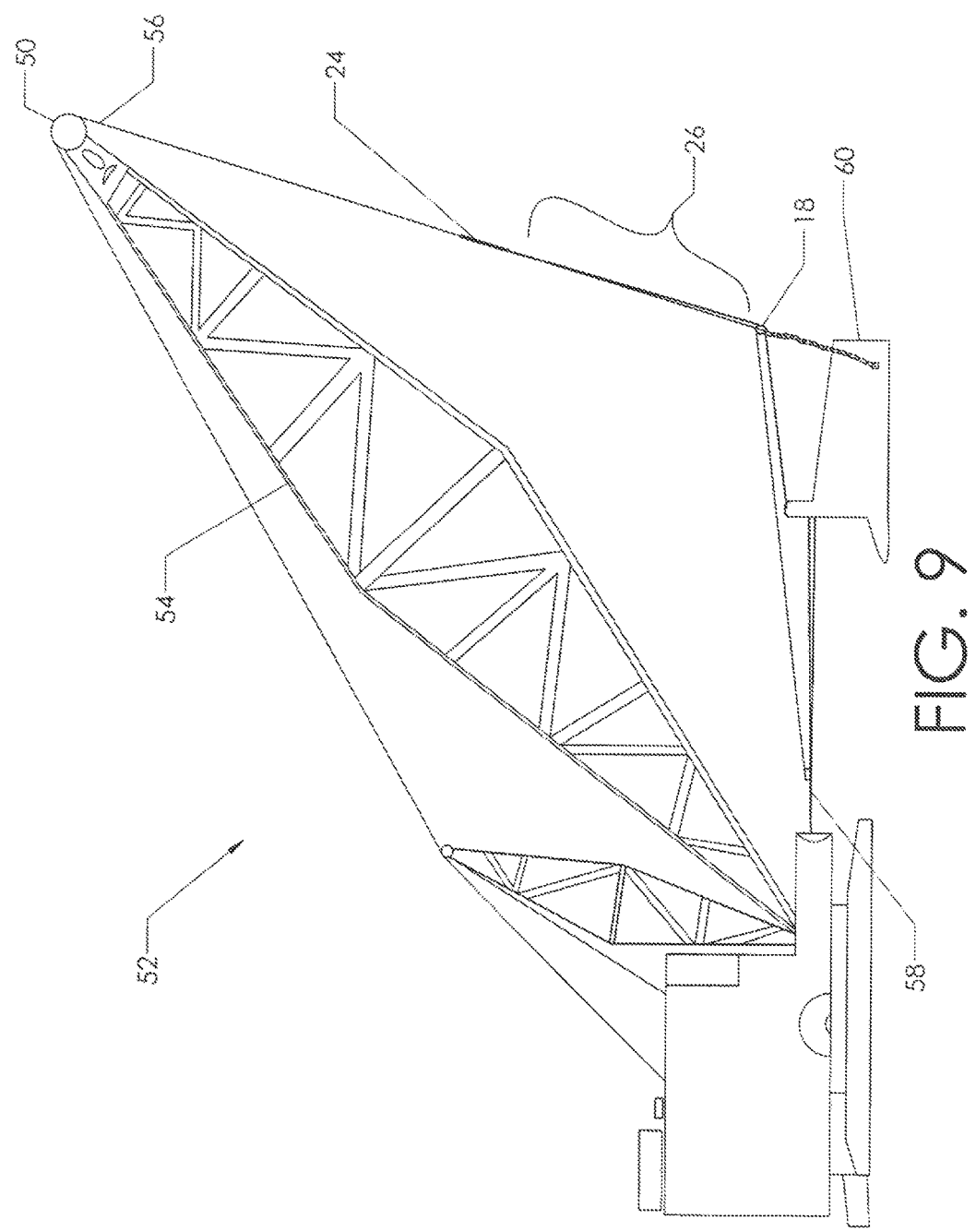
FIG. 9 is an elevation view, showing an inventive cable being used on a dragline crane.

FIG. 9 shows a different application with different selection criteria. Mining dragline crane 52 has a large boom 54 with an attached top sheave 50. Lifting cable 56 passes through top sheave 50 and down to bucket 60. Dragging cable 58 pulls bucket 60 toward the crane's cab during the digging cycle.

In this example interwoven section 24 is located far enough above anchor 18 to prevent its failing into the very hostile environment existing around the bucket and its associated rigging. However, interwoven section 24 is also located low enough so that it is never pulled over top sheave 50 during the normal operation of the dragline crane. Alternatively, the interwoven section might be located so that it always remains between top sheave 50 and the drum located in the body of the dragline crane.

Figure 2:
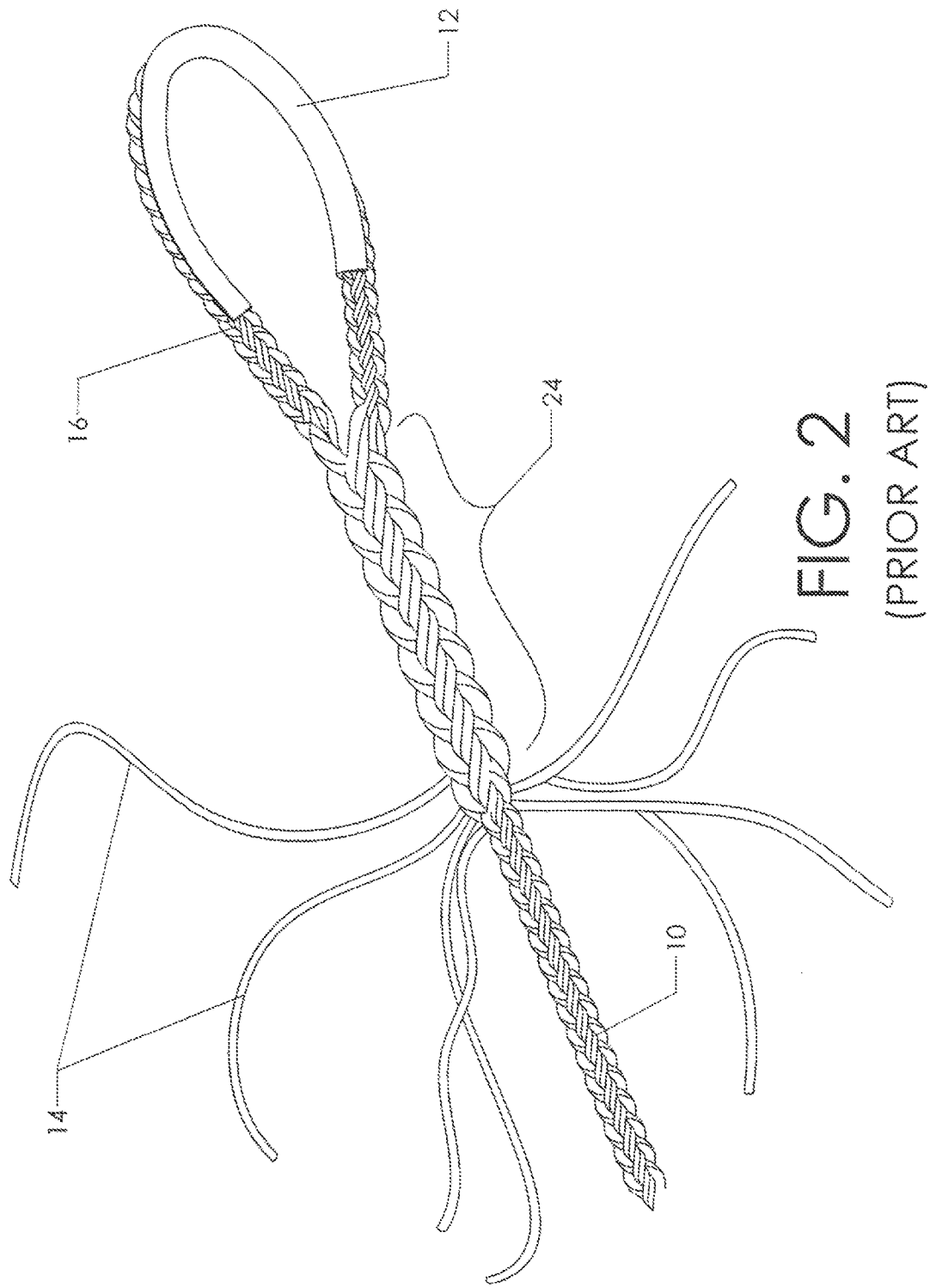
FIG. 2 is a perspective view, showing the continuation of the operation of FIG. 1.

The reader will thereby perceive the advantages offered by a composite cable constructed of a short cable with an attached advanced termination that is connected to a long cable. Additional optional features and combinations include:

1. Attaching a short cable with an advanced termination to both ends of a long cable;
2. Attaching a short cable to a long cable using interlocking eye splices as shown in FIG. 2; and
3. Attaching a short cable to a long cable using other known and trusted techniques.

Although the preceding description contains significant detail, it should not be construed as limiting the scope of the invention but rather as providing illustrations of the preferred embodiments of the invention. Those skilled in the art will be able to devise many other embodiments that carry out the present invention. Thus, the language used in the claims shall define the invention rather than the specific embodiments provided.

I claim:

1. A marine lifting system configured for use in a marine lifting environment where a payload must be lifted above a lower splash boundary in a body of water, comprising:
   (a) a crane having a boom, a tension-carrying drum, and a top sheave;
   (b) a short cable, having a first end and a second end;
   (c) an advanced termination locked to said second end of said short cable;
   (e) wherein said short cable with said advanced termination locked to said second end has passed a defined test criterion by the prior application of a defined test load applied through said advanced termination;
   (f) a long cable, having a first end and a second end;
   (g) wherein said first end of said short cable is joined to said second end of said long cable by an interwoven section, thereby creating a composite cable;
   (h) said composite cable running from said payload over said top sheave and around said tension-carrying drum; and
   (i) wherein a length of said short cable is selected to that said interwoven section is wound onto said tension-carrying drum before said payload is lifted above said lower splash boundary by said crane.

2. The marine lifting system as recited in claim 1, wherein said advanced termination is locked to said second end of said short cable by potting.

3. The marine lifting system as recited in claim 2, wherein a length of said short cable is selected so that said interwoven section and five turns of said short cable are wound onto said tension-carrying drum before said payload is lifted above said lower splash boundary by said crane.

4. The marine lifting system as recited in claim 3, wherein said advanced termination is locked to said second end of said short cable using a two-party epoxy.

5. The marine lifting system as recited in claim 2, wherein said advanced termination is locked to said second end of said short cable using a two-party epoxy.

6. The marine lifting system as recited in claim 2, wherein said short cable and said long cable each comprise eight strands.

7. The marine lifting system as recited in claim 1, wherein said advanced termination is locked to said second end of said short cable using a spike and cone connection.

8. The marine lifting system as recited in claim 7, wherein a length of said short cable is selected so that said interwoven section and five turns of said short cable are wound onto said tension-carrying drum before said payload is lifted above said lower splash boundary by said crane.

9. The marine lifting system as recited in claim 1, wherein a length of said short cable is selected so that said interwoven section and five turns of said short cable are wound onto said tension-carrying drum before said payload is lifted above said lower splash boundary by said crane.

10. The marine lifting system as recited in claim 1, wherein said short cable and said long cable each comprise eight strands.

11. A marine lifting system configured for use in a marine lifting environment where a payload must be lifted above a lower splash boundary in a body of water, comprising:
    (a) a crane having a boom, a tension-carrying drum, and a top sheave;
    (b) a short cable, having a first end and a second end;
    (c) an advanced termination locked to said second end of said short cable;
    (e) wherein said short cable with said advanced termination locked to said second end has passed a defined test criterion by the prior application of a defined test load applied through said advanced termination;
    (f) a long cable, having a first end and a second end;
    (g) wherein said first end of said short cable is joined to said second end of said long cable by a joint, thereby creating a composite cable;
    (h) said composite cable running from said payload over said top sheave and around said tension-carrying drum; and
    (i) wherein a length of said short cable is selected to that said joint resides on said tension-carrying drum before said payload is lifted above said lower splash boundary by said crane.

12. The marine lifting system as recited in claim 11, wherein said advanced termination is locked to said second end of said short cable by potting.

13. The marine lifting system as recited in claim 12, wherein a length of said short cable is selected so that said interwoven section and five turns of said short cable are wound onto said tension-carrying drum before said payload is lifted above said lower splash boundary by said crane.

14. The marine lifting system as recited in claim 13, wherein said advanced termination is locked to said second end of said short cable using a two-party epoxy.

15. The marine lifting system as recited in claim 12, wherein said advanced termination is locked to said second end of said short cable using a two-party epoxy.

16. The marine lifting system as recited in claim 12, wherein said short cable and said long cable each comprise eight strands.

17. The marine lifting system as recited in claim 11, wherein said advanced termination is locked to said second end of said short cable using a spike and cone connection.

18. The marine lifting system as recited in claim 17, wherein a length of said short cable is selected so that said interwoven section and five turns of said short cable are wound onto said tension-carrying drum before said payload is lifted above said lower splash boundary by said crane.

19. The marine lifting system as recited in claim 11, wherein a length of said short cable is selected so that said interwoven section and five turns of said short cable are wound onto said tension-carrying drum before said payload is lifted above said lower splash boundary by said crane.

20. The marine lifting system as recited in claim 11, wherein said short cable and said long cable each comprise eight strands.

\* \* \* \* \*